United States Patent
Van Der Sluis et al.

(10) Patent No.: US 10,232,303 B2
(45) Date of Patent: Mar. 19, 2019

(54) SENSOR SYSTEM AND OXYGEN SEPARATOR COMPRISING A SENSOR SYSTEM

(71) Applicant: KONINKLIJKE PHILIPS N.V., Eindhoven (NL)

(72) Inventors: Paul Van Der Sluis, Eindhoven (NL); Achim Gerhard Rolf Koerber, Eindhoven (NL); Rainer Hilbig, Aachen (DE); Wilhelmus Cornelis Keur, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 121 days.

(21) Appl. No.: 15/105,709

(22) PCT Filed: Dec. 15, 2014

(86) PCT No.: PCT/EP2014/077664
§ 371 (c)(1),
(2) Date: Jun. 17, 2016

(87) PCT Pub. No.: WO2015/091303
PCT Pub. Date: Jun. 25, 2015

(65) Prior Publication Data
US 2016/0310887 A1 Oct. 27, 2016

(30) Foreign Application Priority Data
Dec. 20, 2013 (EP) ..................................... 13198701

(51) Int. Cl.
*B01D 53/02* (2006.01)
*B01D 53/04* (2006.01)
(Continued)

(52) U.S. Cl.
CPC ....... *B01D 53/0454* (2013.01); *B01D 53/047* (2013.01); *G01N 25/482* (2013.01);
(Continued)

(58) Field of Classification Search
CPC .......... B01D 2253/108; B01D 2256/12; B01D 2257/102; B01D 2259/40009;
(Continued)

(56) References Cited

U.S. PATENT DOCUMENTS 3,142,547 A 7/1964 Marsh
3,473,296 A * 10/1969 Tamura ................ B01D 53/047
95/130
(Continued)

FOREIGN PATENT DOCUMENTS

CN 101107513 A 1/2008
CN 104039136 A 9/2014
(Continued)

*Primary Examiner* — Christopher P Jones
(74) *Attorney, Agent, or Firm* — Michael W. Haas

(57) ABSTRACT

The invention relates to an a sensor system (100) for quantitatively detecting at least one compound in a fluid mixture, said fluid mixture comprising the compound to be detected, wherein the sensor system (100) comprises a sorbent material (102) being capable of sorbing the at least one compound to be detected, wherein the sorbent material (102) undergoes a temperature change when sorbing the at least one compound; at least a first temperature sensor (104) for measuring the temperature of the sorbent material (102); and a control unit (110) being adapted for quantitatively determining the at least one compound to be detected based on the temperature change of the sorbent material (102). Such a sensor system (100) provides an improved measurement especially in the field of oxygen concentrators. The invention further relates to an oxygen concentrator (10) for generating oxygen enriched gas as well as to a method of
(Continued)

quantitatively detecting at least one compound in a fluid mixture.

10 Claims, 3 Drawing Sheets

(51) Int. Cl.
*G01N 25/48* (2006.01)
*B01D 53/047* (2006.01)
(52) U.S. Cl.
CPC ... *G01N 25/4873* (2013.01); *B01D 2253/108* (2013.01); *B01D 2256/12* (2013.01); *B01D 2257/102* (2013.01); *B01D 2259/40009* (2013.01); *B01D 2259/4533* (2013.01)
(58) Field of Classification Search
CPC ........ B01D 2259/4533; B01D 53/0454; B01D 53/047; G01N 25/482; G01N 25/4873
See application file for complete search history.

(56) References Cited

U.S. PATENT DOCUMENTS

| | | | |
|---|---|---|---|
| 3,533,221 A | 10/1970 | Tamura | |
| 4,916,630 A | 4/1990 | Miller | |
| 6,080,226 A * | 6/2000 | Dolan | B01D 53/02 95/100 |
| 6,233,925 B1 * | 5/2001 | Hirota | F01N 3/0233 60/285 |
| 6,372,026 B1 * | 4/2002 | Takemasa | B01D 53/0423 96/112 |
| 7,329,304 B2 | 2/2008 | Bliss | |
| 7,445,663 B1 | 11/2008 | Hunter | |
| 2005/0061148 A1 * | 3/2005 | Johansson | B01D 53/0462 95/128 |
| 2005/0109081 A1 | 5/2005 | Zribi | |
| 2005/0235831 A1 * | 10/2005 | Taveira | A61M 16/009 96/111 |
| 2008/0116071 A1 | 5/2008 | Nakamura | |
| 2009/0183498 A1 * | 7/2009 | Uchida | F01N 3/0835 60/288 |
| 2010/0242734 A1 * | 9/2010 | Maeda | A61M 16/10 96/110 |
| 2012/0272966 A1 * | 11/2012 | Ando | A61M 16/10 128/205.27 |
| 2013/0209315 A1 | 8/2013 | Kimura | |
| 2013/0233168 A1 | 9/2013 | Richey, II | |
| 2014/0020685 A1 * | 1/2014 | Szabo | A61M 16/009 128/203.29 |
| 2015/0004677 A1 | 1/2015 | Kay | |

FOREIGN PATENT DOCUMENTS

| | | |
|---|---|---|
| DE | 4132034 A1 | 4/1993 |
| EP | 1029577 A2 | 8/2000 |
| EP | 1114666 A2 | 11/2001 |
| JP | 6153555 A | 3/1986 |
| JP | 63080823 A | 4/1988 |
| JP | 2000087732 A | 3/2000 |
| JP | 2009039686 A | 2/2009 |
| WO | WO2009105597 A1 | 8/2009 |
| WO | WO2013038299 A1 | 3/2013 |
| WO | WO2013038315 A1 | 3/2013 |

* cited by examiner

SENSOR SYSTEM AND OXYGEN SEPARATOR COMPRISING A SENSOR SYSTEM

CROSS-REFERENCE TO RELATED APPLICATIONS

This patent application claims the priority benefit under 35 U.S.C. § 371 of international patent application no. PCT/EP2014/077664, filed Dec. 15, 2014, which claims the benefit of European Patent Application No. EP13198701.8, filed on Dec. 20, 2013, which is hereby incorporated by reference herein.

FIELD OF THE INVENTION

The invention relates to sensor systems. The invention particularly refers to sensor systems being usable, for example, in the field of oxygen separation.

BACKGROUND OF THE INVENTION

Sensors for detecting gases are used in different applications. Often, gas sensors are required to be highly sensitive and cost-effective to build as well as to use. As an example, gas sensors may be used in oxygen concentrators adapted for oxygen therapy in order to control process conditions.

Oxygen therapy is the administration of oxygen as a therapeutic modality. It is widely used for a variety of purposes in both chronic and acute patient care as it is essential for cell metabolism, and in turn, tissue oxygenation is essential for all physiological functions. Oxygen therapy should be used to benefit the patient by increasing the supply of oxygen to the lungs and thereby increasing the availability of oxygen to the body tissues, especially when the patient is suffering from hypoxia and/or hypoxemia. Oxygen therapy may be used both in applications in hospital or in home care. The main home care application of oxygen therapy is for patients with severe chronic obstructive pulmonary disease (COPD).

Oxygen may be administered in a number of ways. A preferable way of oxygen administration is by using a so called on demand generation of oxygen. Referring to this, commercial solutions, so-called oxygen concentrators or separators, respectively, are widely known. These oxygen concentrators mostly separate oxygen from an oxygen comprising gas, so that the oxygen is provided on demand, i.e. directly before use.

Known from EP 1 029 577 A2 is an apparatus for producing oxygen enhanced gas from air. According to this document, fractionators produce an oxygen enhanced gas for use in oxygen inhalation therapy. The fractionators include an air source for supplying air, and a plurality of columns for containing an adsorbent material for adsorbing nitrogen gas. Each of the columns has first and second ends. Air is directed from the air source to the column through the first open ends of the respective columns. A temperature sensor detects the temperature of the side wall of one of the columns. The fractionators changes the time for adsorption of nitrogen gas to the adsorbent material based on the detected temperature.

There is, however, still potential for improving the operating conditions of oxygen separation devices especially with regard to measuring oxygen purity.

SUMMARY OF THE INVENTION

It is an object of the present invention to provide a sensor system which is cost-saving to build and to use, which has a good sensitivity and/or which is particularly well suitable for oxygen concentrators.

This object is achieved by a sensor system according to claim 1. This object is furthermore achieved by an oxygen concentrator according to claim 9 as well as by a method for detecting at least one compound according to claim 11. Preferred embodiments are defined in the dependent claims.

A sensor system is provided for quantitatively detecting at least one compound in a fluid mixture, said fluid mixture comprising the compound to be detected. The sensor system comprises a sorbent material being capable of sorbing the at least one compound to be detected, wherein the sorbent material undergoes a temperature change when sorbing the at least one compound; at least a first temperature sensor for measuring the temperature of the sorbent material; and a control unit being adapted for quantitatively determining the at least one compound to be detected based on the temperature change of the sorbent material.

A sensor system like described above provides for a high sensitivity as well as cost-efficient producibility as well as usability and may thereby be particularly suitable for determining the purity of an oxygen comprising gas. The sensor system will thus be particularly described with regard to an oxygen concentrator, or oxygen separator, respectively. It is, however, explicitly stated that the sensor system is not limited to an application in the field of oxygen separation, like will be apparent without any doubt for one skilled in the art.

In detail, the sensor system as described above comprises a sorbent material which is capable of sorbing at least one compound to be detected. A sorbent material may thereby be understood as a material which sorbs and thus adsorbs or absorbs at least one compound from a fluid mixture, such as a gaseous mixture or a mixture comprising one or more gases and one or more liquids, much better than at least one further compound of that mixture. The compound to be detected thus preferably is a fluid such as a gaseous compound or a liquid compound. Advantageously, the sorbent material is highly selective with regard to the compound to be detected and sorbs this compound much more effective at least with regard to further compounds being present in the fluid mixture such as the gaseous mixture.

The sorbent material is thereby selected with regard to the compound to be detected such, that the sorbent material undergoes a temperature change when sorbing the compound to be detected. This is generally a well-known effect for sorbent materials. In fact, depending on the adsorption enthalpy, for example, of the compound to be detected together with the state of the sorbent material and thus, if further compounds are sorbed thereto, due to a sorption process, the temperature of the sorbent material may change. This temperature change particularly together with its magnitude is thereby dependent on the amount of compound being sorbed and thus on the concentration of the respective compound in the atmosphere surrounding the sorbent material formed by the fluid mixture.

The sensor system is thus based on the finding that in case a sorbent material sorbs a defined compound, such a process will be accompanied with a temperature change of the sorbent material, such as mostly by a temperature rise. Therefore, the temperature change together particularly with its magnitude may be used as an indicator of which and how much compound is sorbed to the sorbent material. Therefore, the temperature change may be used as a qualitative and further as a quantitative indicator of the compound of interest being present in the atmosphere surrounding the sorbent material and thus in the fluid mixture to be analyzed.

Due to the fact that the sensor system is based on a sorption process of the compound of interest to the sorbent material, the sorbent material may be present in the atmosphere, or the fluid mixture, respectively, to be analyzed. In order to detect a compound in a gas stream, for example, at least the sorbent material may be located inside a respective gas conduit.

Even though gaseous mixtures may be preferred applications for the sensor system, it is however apparent that the sensor system is not limited to gaseous mixtures. In fact, depending on the compound to be detected as well as on the sorbent material being appropriate, the sensor system may as well be usable, for example, in order to detect further fluids, such as water.

In order to measure the temperature change of the sorbent material, at least a first temperature sensor for measuring the temperature of the sorbent material is provided. Such a temperature sensor may generally be any temperature sensor known in the art insofar it is suited to measure the temperature of the sorbent material. Therefore, the temperature sensor may be provided in direct thermal contact with the sorbent material, or it may measure the respective temperature by radiation, such as infrared radiation, for example. Thus, it may be appropriate but not strictly required that the temperature sensor is provided in direct vicinity to the sorbent material and thus together with the sorbent material as well in the atmosphere, or the fluid mixture, respectively, to be analyzed, in order to measure the temperature change of the sorbent material especially effectively and accurate. The first temperature sensor together with the sorbent material may thereby be formed as a compact uniformal constructional element.

Further, in order to correlate the measured temperature change of the sorbent material, a control unit is provided, the control unit being adapted for quantitatively determining the at least one compound to be detected based on the temperature change of the sorbent material. According to this, the control unit may comprise, for example, a memory in which memory a lookup table is present, which lookup table gives information about temperature changes which correspond to respective concentrations or concentration changes of compounds to be detected. Thus, the lookup table may be prepared by calibrating the control unit by measuring the dependence of a temperature change with regard to defined concentrations or concentration changes of the compound to be detected and thus of respective sorption processes.

Such a sensor system like described above provides a plurality of advantages with regard to the solutions according to prior art.

In fact, the sensor system like described above is producible in a very cost-effective manner due to the fact that the components required are no cost-intense complex parts but in contrast thereto may be provided without significant costs. In detail, the sorbent material required is known in the art for many different applications and has no significant production costs. Further, the temperature sensor to be used is further as well no complex and cost-intense part and may be provided cost-saving as a mass produced article either. As a control unit may be present in most applications, it becomes clear that no complex installations have to be prepared.

Furthermore, the sensor system may easily be adapted to the compound to be detected as well as to the fluid mixture used. This is due to the fact that solely the sorbent material has to be exchanged such, that an appropriate selectivity and sensitivity with regard to the compound to be detected may be reached. It is thus simply a matter of studying reference materials to identify the sorbent material which is appropriate for the desired application. The sensor system may be calibrated with regard to the used sorbent material and the compound to be detected in order to generate an appropriate lookup table, after which calibration, for example, the sensor system may work immediately. Therefore, the sensor system may work for each required application without further complicated installations.

Next to that, the sensor system may detect a respective compound with a high sensitivity being suitable for many different applications, such as, for example, in the field of oxygen concentration. In detail, especially in case the sorbent material has a high selectivity to the compound to be detected with regard to further compounds present in the atmosphere surrounding the sorbent material, a sorption process may lead to a significant and well detectable temperature change already in case only slight amounts of the compound to be detected are sorbed. Therefore, a highly sensitive measurement may be possible.

Apart from that, a temperature change of the sorbent material is an effect which accompanies the sorption process instantaneously, so that the measurement of the compound to be detected as well is possible very dynamic and thus essentially without any time delay. Therefore, in case the controlling of a process is dependent on the result of the respective measurement, the controlling may be performed especially dynamic allowing a fast answer to changing conditions.

The above described very dynamic measurement may be even improved in case the sensor is made very small and thus with as less sorbent material as possible. Due to this, the heat capacity and thus the time delay of its response may be further reduced.

Furthermore, the working principle of the sensor system allows a very energy saving behavior due to the fact that a temperature sensor as such may be used without large energy consumption and apart from potential regeneration steps, a sorption process does as well not require large exterior energy. Therefore, the sensor system may be particularly suitable for portable applications.

To summarize, the sensor system like described above allows a sensitive and dynamic process for quantitatively detecting a compound in a fluid mixture, such as a gas mixture.

According to an embodiment, the sensor system further comprises a second temperature sensor for measuring the temperature of the fluid mixture, wherein the control unit is adapted for quantitatively determining the at least one compound to be detected based on the temperature change of the sorbent material relative to the magnitude of the temperature change of the fluid mixture.

According to this embodiment, the detection of the compound of interest may be reached in an especially exact and accurate manner. In fact, according to this embodiment, it is avoided that the determination of the compound to be detected is based on a temperature change and particularly its magnitude of the sorbent material that is not only due to a sorption process of the respective compound to the sorbent material but that is as well due to other effects. In fact, apart from the chemical effect of the sorption process, also pressure changes, for example, may induce thermal effects into the sorbent material because of adiabatic heating and cooling. To compensate for these purely physical effects, the second temperature sensor is provided which second temperature sensor is adapted for measuring the temperature of the fluid mixture, such as a gas or the atmosphere surrounding the sorbent material, respectively. Therefore, temperature changes not strictly being due to sorption processes may be determined and may be taken into consideration when determining the concentration of the gas to be detected based on the measurement of the first temperature sensor. This allows preventing deteriorating the measurement results due to undesired temperature influences to the sorbent material. As a result, a sensor system according to this embodiment may be especially reliable and especially exact.

According to a further embodiment, the sorbent material is provided on a surface of the first temperature sensor. Particularly, the sorbent material may be provided on the surface of an active part of the temperature sensor. In other words, the active part of the first temperature sensor and thus the part which measures the temperature is in direct contact to the sorbent material. For example, the sorbent material may be coated onto the surface of the temperature sensor. In a non-limiting example, the sorbent material may be glued to the surface of the temperature sensor. With this regard, a glue may be used which has an especially well heat conductance in order not or not significantly deteriorating the temperature measurement. According to this embodiment, an especially close thermal contact may be provided between the sorbent material and the temperature sensor. Therefore, a temperature change of the sorbent material may be detected by the temperature sensor especially fast allowing especially dynamic measurements. As a result, depending on the respective application of the sensor system, a very dynamic answer with regard to the results of the measurements may be allowed. Further, the first temperature sensor provided with the sorbent material may be designed as a compact part together with the sorbent material which may easily be exchangeable with regard to desired applications.

According to a further embodiment, at least one of the first temperature sensor and the second temperature sensor comprises a thermistor a thermocouple. Especially a thermistor is a temperature sensor which is well applicable for the sensor system like described above due to highly advantageous synergistic effects. In detail, a thermistor may be understood as a sensor which is a type of resistor whose resistance varies significantly with temperature. Therefore using a thermistor, the temperature may be detected by measuring a current, or a resistance, respectively of the resistor. It is thereby easily possible to place the sorbent material in vicinity to the resistor in order to provide a close thermal contact between the sorbent material and the thermistor and thus the sensor. As an example, the resistor may directly be coated with the sorbent material in order to allow an especially effective heat measurement. Apart from that, a thermistor is mostly very stable against a plurality of working conditions allowing a very high reliability and lifetime. Thus, a thermistor may be usable, for example, very well in the field of oxygen separation. Apart from that, a thermistor is furthermore very cost-effective. As an example, a suitable thermistor may be based on platinum as active part and may exemplarily be the one purchased under its name PT 1000 from the company Labfacility. However, generally every thermistor withstanding the conditions used may be appropriate.

With regard to a thermocouple, this is particularly a temperature-measuring device which comprises two particularly dissimilar conductors that contact each other at one or more spots. In case the temperature of one of the spots differs from the reference temperature at other parts of the circuit, a voltage is applied. Therefore, a thermocouple may be especially advantageous in case a first and a second temperature sensor is provided. This is due to the fact that if properly connected for example reversely, two parts of the thermocouples can give the temperature difference between sensor and reference directly. Accordingly, a temperature change will only be detected in case there is a difference between the sorbent material and the fluid mixture because of which undesired temperature influences for example due to pressure changes are not to be considered.

According to a further embodiment, a heating device is provided for heating the sorbent material. According to this embodiment, it may be counteracted to the effect according to which the sorbent material after a certain time of measuring t may be contaminated with contaminants potentially being present in the gas to be detected, such as in a non-limiting manner water or carbon dioxide, being sorbed to the sorbent material resulting in a decrease of sensitivity. Due to the provision of a heating element, the sorbent material may be regenerated by heating it to a temperature, for example, in the range of 300-500° C., in order to again improve the sensitivity. The heating element may comprise, for example, heating wires which are located in direct vicinity to the sorbent material, or may proceed, for example, there through.

According to a further embodiment, the sorbent material is a zeolite. Particularly, the sorbent material may include sodium or lithium LTA or FAU framework zeolites, for example the Li-LSX faujasite sorbent material being purchasable under its name SXSDM from the firm CECA. Another example may comprise a 5A-type zeolite, for example. These sorbent materials are very beneficial with regard to sorbing desired compounds, for example nitrogen, and further for showing a temperature effect when sorbing the respective compound. It has however be noted that the sorbent material chosen may be selected in dependence of the compound to be detected as well as the mixture the compound is present in.

According to a further embodiment, the sorbent material is capable of sorbing nitrogen. Therefore, the sensor system may particularly act as a nitrogen sensor making it particularly suitable in the field of oxygen separation, such as being a part of an oxygen concentrator, like will be apparent down below.

With respect to further advantages and technical features of the sensor system it is referred to the description of the oxygen concentrator, the method, the figures and the description of the figures.

The present invention further relates to an oxygen concentrator for generating oxygen enriched gas, wherein said oxygen concentrator comprises a sensor system like described above.

An oxygen concentrator according to the present invention is a device which is capable of using a gas mixture, such as air, and generating a gas which comprises a higher amount of oxygen compared to the initial gas mixture. In an exemplary embodiment, the oxygen concentrator may comprise at least one oxygen separation device. The oxygen concentrator may thereby comprise only one oxygen separation device or preferably a plurality of more than one oxygen separation devices. For example, the oxygen concentrator may comprise two oxygen separation devices and may thus generally form a pressure swing adsorption system (PSA system). However, the oxygen concentrator may as well form a vacuum swing adsorption system (VSA) or a vacuum pressure swing adsorption system (VPSA), for example.

For separation purposes and in an exemplary embodiment, an oxygen separation device comprises, or is filled with, respectively, an oxygen separation sorbent for separating oxygen from an oxygen comprising gas. Thus, the oxygen separation device may form a sieve bed. The oxygen separation sorbent is thereby capable of separating oxygen from an oxygen comprising gas by sorbing at least one compound of the oxygen comprising gas apart from oxygen or at least better than oxygen. This feature is in accordance with the general setup of a pressure swing adsorption system according to which a separation sorbent interacts with at least one compound of the oxygen comprising gas with the exception of oxygen or better than oxygen and thus lets oxygen pass. This feature allows for at least temporarily immobilizing one or more compounds of the oxygen comprising gas resulting in a separation of oxygen from further compounds of the oxygen comprising gas. For example, the oxygen separation sorbent may be designed for adsorbing nitrogen but does less or not interact with oxygen in order to let the oxygen pass through and to generate a flow of pure or essentially pure oxygen, or of oxygen enriched gas, respectively, when guiding a flow of oxygen comprising gas, such as particularly air, through the latter.

Non limiting examples for oxygen separation sorbents include zeolites, such as sodium or lithium LTA or FAU framework zeolites, for example the Li-LSX faujasite sorbent material being purchasable under its name SXSDM from the firm CECA.

In order to guide oxygen comprising gas to the oxygen separation device, the oxygen separation device, especially each oxygen separation device present, comprises a gas inlet at a primary side being connected to an inlet conduct for guiding a flow of oxygen comprising gas into the oxygen separation device and a gas outlet at a secondary side being connected to an outlet conduct for guiding a flow of oxygen enriched gas out of the oxygen separation device.

The gas flow, in particular the flow of oxygen comprising gas into the oxygen separation device and the flow of oxygen enriched gas out of the oxygen separation device, may thereby be reached by providing a gas conveying device which creates a pressure difference between the primary side and the secondary side of the oxygen separation device. The gas conveying device may for example be a compressor being positioned on the primary side of the oxygen separation device, and/or it may be formed as a vacuum pump being positioned on the secondary side of the oxygen separation device.

Next to creating a pressure difference between the primary and the secondary side of the oxygen separation device, the gas conveying device may thus be useful for conveying the oxygen comprising gas from a source of oxygen comprising gas to the gas inlet, through the oxygen separation device and the generated oxygen through the outlet conduct. This step is especially performed in case the oxygen separation device generates oxygen and is thus in an oxygen separation mode, or in a feed mode, respectively.

It is however known for oxygen separation devices, and their oxygen separation sorbents, respectively, that after a certain time of usage, the sorbent material has to be regenerated in order to desorb the sorbed materials, such as particularly nitrogen. Therefore, it is known to operate the oxygen concentrator, or the oxygen separation device, respectively, in a purge mode by conveying a purging gas through the oxygen separation device. Therefore, the secondary side of the oxygen separation device, for example the gas outlet of the oxygen separation device, is preferably connected to a source of purging gas for guiding purging gas through the oxygen separation device to the primary side, and the primary side of the oxygen separation device, for example the gas inlet of the oxygen separation device, is preferably connected to an exhaust conduct for guiding exhaust gas out of the oxygen separator.

Therefore, an oxygen separator thus separates an oxygen comprising gas such as air essentially into nitrogen and oxygen in a cyclic mode of operation. In a first phase of the cycle the oxygen comprising gas is fed as "inflow" into the oxygen separation device at a higher pressure feed, nitrogen is kept such as adsorbed within this device and pure oxygen is collected as outflowing "product". In a second phase of the cycle the separation device is regenerated, i.e. a purge gas such as a part of the produced oxygen enriched gas, for example, is fed back into the device at a lower pressure purge and the previously adsorbed nitrogen is released as "exhaust" into the surrounding atmosphere. For example at least two separation devices filled with suitable selectively oxygen separation sorbent are used: while one device is in the "feed" phase producing oxygen enriched gas at higher pressure, the other device, being in the "purge" phase at lower pressure, is regenerated with part of the oxygen flow produced by the first device, for example. After a certain time respectively arranged valves are switched and both devices change their role.

A well-known requirement for using oxygen concentrators is the adaptation of the process to varying process conditions, such as ambient temperature, ambient pressure, actual demand of oxygen flow and/or status of the individual separation devices. Therefore, oxygen concentrators may be controlled by an electronic control unit preferably comprising a microcontroller.

Inventors have surprisingly found that by providing a sensor system like described above in the oxygen concentrator for determining the concentration of at least one particularly gaseous compound, the detection of compounds in a gas stream generated by the oxygen concentrator may be especially advantageous and thus the controlling of the oxygen concentrator and thus the purity and quality of the oxygen enriched gas generated may significantly be enhanced.

In fact, in conformance with the description of the sensor system above and with regard to its application in an oxygen concentrator, the sensor system may exemplarily be a nitrogen sensor and may have a working principle being based on the fact that the sorbent material used in the sensor system has a higher affinity for nitrogen ($N_2$) compared to oxygen ($O_2$). Accordingly, when a particularly oxygen-saturated sorbent material is subjected to nitrogen gas it will sorb the nitrogen and desorb oxygen. This is accompanied by a thermal effect because of which the temperature of the sorbent material rises. Accordingly, the sensor system like described above is very well suited for measuring the nitrogen concentration and thus the oxygen purity of an oxygen enriched gas, for example.

Thereby, the application of a sensor system like described above may be especially preferred due to the fact that the sorbent material used for sorbing the substance to be detected may be the same compared to the oxygen separation sorbent used in the oxygen separation device. Therefore, a deterioration of the oxygen separation process may be avoided likewise a deterioration of the measurements due to the oxygen separation devices.

Apart from that, due to the fact that the oxygen separation sorbent generally is adapted to the respective properties of the gaseous mixture it comes in contact to, there is no risk of the sorbent material of the sensor system to be instable against the properties being present. Therefore, the reliability as well as the lifetime of the sensor system is not problematic.

A controlling of the oxygen concentrator for example with regard to the speed of the pressure adjusting device, to the adjustment of the timing of the feed and purge phases, to a step of counteracting imbalances between a plurality of separation devices, may be realized especially effective. This additionally allows the purity of the generated oxygen enriched gas to be further improved. The respective control unit may thereby be the same described with respect to the sensor system.

Preferably, the oxygen separator is formed as a portable device. Essentially, according to the invention, portable could mean a fully independent and self-contained embodiment. Such an embodiment in turn means that no connections, such as to a power source or to a source of oxygen comprising gas, are required during use to further compounds next to the oxygen separator as such. Especially, no connections to stationary elements are required during use and thus during generating oxygen. Such a portable device may have a grip for carrying it or it may be arranged in a carrying device, such as a bag and it may be equipped with an energy source, for example. Especially portable oxygen concentrators are sensitive against influences of operating conditions because of their limited space of the oxygen separation device, or the limited amount of oxygen separation material, respectively. For example, with respect to portable oxygen concentrators, influences such as impurities of the oxygen separation material, altering working temperatures and the like may under circumstances quickly lead to decreased oxygen selectivity, for example which may require a dynamic controlling of the latter. Consequently, the oxygen separator according to the invention is especially advantageous for portable devices or for devices comprising a small oxygen separation device and/or a limited amount of oxygen separation material.

According to an embodiment of the oxygen concentrator, at least the sorbent material of the sensor system is provided in an equalization conduit. Preferably, the sorbent material together with the temperature sensor is located in the equalization conduit. An equalization conduit is thereby a conduit, or duct, respectively, which may be provided in case more than one oxygen separation device is provided. It is located at the product side of the oxygen separation devices and connects the latter at their product sides. It may be provided with valves in order to close it during normal operation for example during a purge phase or a feeding phase. The object of an equalization conduit is to allow an equalization phase during the oxygen separation cycle. In detail, the efficiency of a Pressure-Swing-Adsorption (PSA) cycle, for example, is increasing if part of the compressed-air energy stored in the first device after the feed phase is re-used for pressurizing the second device to an intermediate pressure. To this purpose a short equalization phase, during which both devices are connected at their product side via said equalization conduit, is inserted between the main phases of the operating cycle.

According to this embodiment, it is profited from the effect that despite of minor impurities such as argon, for example, in the equalization conduit the oxygen enriched gas and thus nearly pure oxygen may be present when the process is running at desired conditions. When the process is deviating from these ideal conditions, the nitrogen concentration will rise which is directly detectable by the sensor system like described above. Further, the maximum concentration of nitrogen in the equalization phases is typically a factor of two to three higher compared to the nitrogen concentration in the product gas such as in a product tank. Furthermore, the gas volumes exchanged between the separation devices in the equalization phases are typically a factor of two larger than the gas volumes exiting from the separation devices in the product phases.

Therefore, the proposed diagnostics comprising a sensor system in the equalization conduit is more sensitive and faster than other process diagnostics—e.g. based on the oxygen content of the product only. In fact, the oxygen content of the equalization conduit, compared to an oxygen content in a product gas and thus the oxygen enriched gas, e.g. such as measured by an oxygen sensor in the product tank like known in the art, is in practice reacting much faster on changes in the process. Further, the maximum pressure within a separation device as measured a pressure sensor in the product conduit or tank gives in practice a more unspecific or less sensitive signal compared to a gas measurement in the equalization conduit so that according to this embodiment, a more reliable controlling of the process may be achieved.

In other words, the resulting signal of the sensor system in the equalization conduit enables especially reliable process diagnostics to control the separation process, for example to avoid a breakthrough of the nitrogen front into the product stream, to avoid fluctuations of the oxygen purity of the product and/or eventually to minimize the needed power input.

With respect to further advantages and technical features of the oxygen concentrator it is referred to the description of the sensor system, the method, the figures and the description of the figures.

The present invention further relates to a method of quantitatively detecting at least one compound in a fluid mixture, said fluid mixture comprising the compound to be detected, wherein the method comprises the steps of: sorbing the compound to be detected to a sorbent material, wherein the sorbent material undergoes a temperature change when sorbing the at least one compound; measuring the temperature of the sorbent material; and quantitatively detecting the at least one compound based on the temperature change of the sorbent material.

Such a method is thus suitable for quantitatively detecting at least one particularly fluid, i.e. gaseous or liquid, compound in a fluid compound mixture or in other words for determining the concentration or a change of concentration of the compound of interest. In particular, this method is suitable for detecting the concentration or a concentration change of one compound of interest in a compound mixture. Particularly, this method is advantageous for use in an oxygen concentrator. This method may be used, for example, for detecting nitrogen in an oxygen atmosphere. The method may however further used to detect a fluid concentration or respective concentration changes in a gas. An example would be the detection of water in a gas such as in oxygen or in a noble gas. This method has significant advantages with regard to which it is referred to the respective description of the sensor system. To summarize, this method provides an energy saving, cost-effective, easily adaptable and/or fast measure to provide a sensitive detection of the component of interest. It thus allows controlling of processes, such as in the field of oxygen separation, to be very dynamic and effective.

According to an embodiment, the at least one compound is quantitatively detected based on the temperature change of the sorbent material relative to a temperature change of the fluid mixture. According to this embodiment, the detection of the compound of interest may be reached in an especially exact and accurate manner due to the fact that it is avoided that the temperature change of the sorbent material is not only due to a sorption process of the respective compound but that the temperature change may as well be due to other effects, thus potentially deteriorating the measurements.

According to a further embodiment, the method is part of a method for separating oxygen from an oxygen comprising gas.

Such a method for separating oxygen may generally comprise, according to a first step, an oxygen separation step, wherein the oxygen separation step comprises guiding an oxygen comprising gas to the primary side of one or more oxygen separation devices, and generating a flow of oxygen through the oxygen separation device or devices by creating a pressure difference, for example by a compressor or by a vacuum pump between the primary and secondary side. This step thus corresponds to a generally known oxygen separation step using an oxygen separator in which an oxygen comprising gas is guided into an oxygen separation device in which further constituents apart from oxygen are sorbed to an oxygen separation sorbent and oxygen is guided out of the oxygen separation device.

In order to desorb sorbed substances from the one or more before used oxygen separation devices, or its oxygen separation sorbent, respectively, the at least one oxygen separation device is purged after the oxygen separation step by guiding a purging gas through the oxygen separation device from its secondary side to its primary side, and by guiding exhaust gas through the exhaust conduit. This regeneration step may as well be performed by a gas conveying device such as a compressor or a vacuum pump and is thus a conventional step known from pressure swing adsorption systems, for example.

Furthermore, the method may comprise the further step which in a generally matter may be performed during one or more of the before described steps or as a separate step. According to this step, at least one compound is determined like described above by using a sensor system like described above by sorbing the compound to be detected to a sorbent material, wherein the sorbent material undergoes a temperature change when sorbing the at least one compound, wherein the temperature of the sorbent material is measured and wherein the at least one compound is quantitatively detected based on the temperature change of the sorbent material.

According to a further embodiment, the at least one compound is detected during an equalization phase and thus particularly in an equalization conduit. According to this embodiment, it is profited from the effect that despite of minor impurities such as argon, for example, in the equalization conduit pure oxygen may be present when the process is running at desired conditions. When the process is deviating from these ideal conditions, the nitrogen concentration will rise which is directly detectable by the sensor system like described above. Further, the maximum concentration of nitrogen in the equalization phases in the equalization conduit is typically a factor of two to three higher compared to the nitrogen concentration in the product gas such as in a product tank. Furthermore, the gas volumes exchanged between the separation devices in the equalization phases are typically a factor of two larger than the gas volumes exiting from the separation devices in the product phases. Therefore, the proposed equalization sensor diagnostics is more sensitive and faster than other process diagnostics—e.g. based on the oxygen content of the product only.

With respect to further advantages and technical features of the method of generating oxygen it is referred to the description of the oxygen separator, the figures and the description of the figures.

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

Figure 1:
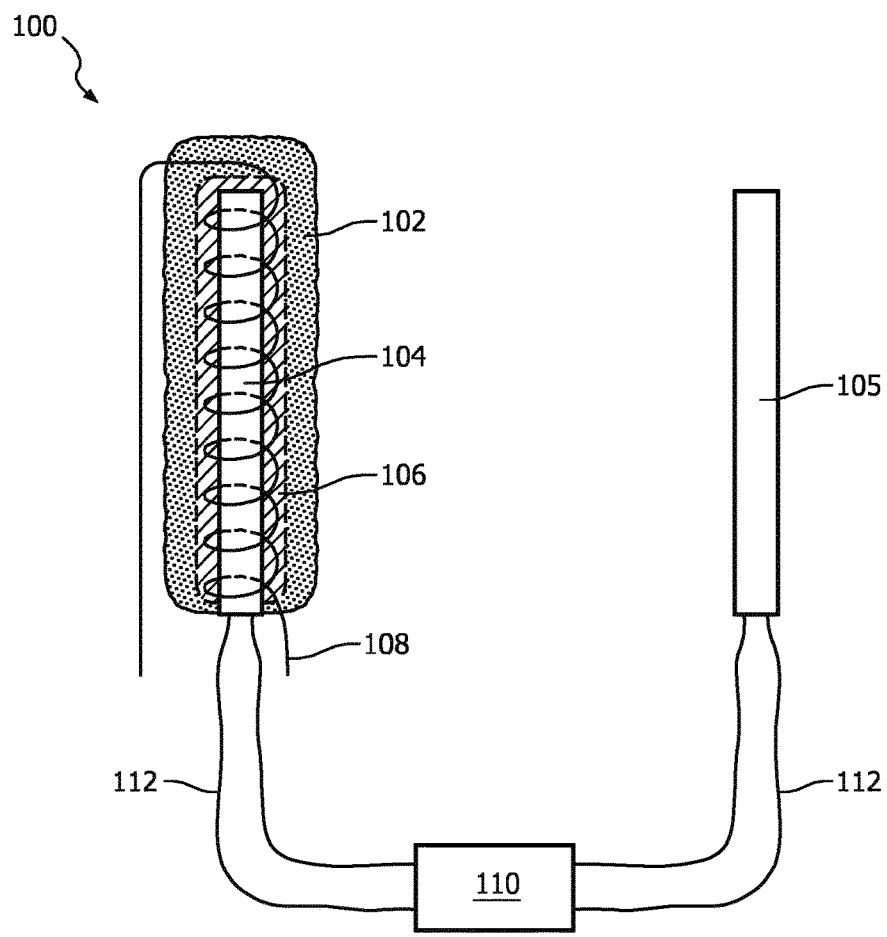
FIG. 1 shows a schematic view of an embodiment of a sensor system according to the invention.

In FIG. 1, a sensor system 100 is shown which is usable for quantitatively detecting at least one compound in a fluid mixture. As a non-limiting example, the sensor system 100 may be used in an oxygen concentrator 10 like will be apparent with regard to FIG. 2.

The sensor system 100 comprises a sorbent material 102 being capable of sorbing the at least one compound to be detected. The sorbent material 102 is thereby selected such, that it undergoes a temperature change when sorbing the at least one compound. For example, the sorbing material 102 may be a zeolite material.

The sensor system 100 further comprises at least a first temperature sensor 104 for measuring the temperature of the sorbent material 102. The temperature sensor 104 may for example be a thermistor. With regard to the first temperature sensor 104 shown in FIG. 1, the sorbent material 102 is provided on a surface of the first temperature sensor 104. It may be fixed, for example, by means of a glue 106, such as a water based high temperature cement. As a strictly exemplarily and non-limiting example, the glue called Hydra from the company Griffon may be used. Further, a heating device may be present which may be used for heating and thus regenerating the sorbent material 102. Shown in FIG. 1 is a heating wire 108 which proceeds through the sorbent material 102 and further through the glue 106. The heating wire 108 may be a kanthal wire.

Preferably, the sensor system 100 further comprises a second temperature sensor 105 for measuring the temperature of the fluid mixture. A control unit 110 is further provided which is adapted for determining the concentration of the at least one compound to be detected based on the temperature change of the sorbent material 102 alone or preferably relative to the temperature change of the fluid mixture.

The temperature sensors 104, 105 may be connected to the control unit by connections 112, which may serve for using the temperature sensors 104, 105 for example by measuring respective resistivities.

Particularly in case the sensor system 100 is handled in air and by using a glue which is water based, such as a water based high temperature cement, the sorbent material 102 which may have a high affinity for water may be saturated with water and will then be not or only very little sensitive to nitrogen. Due to this, the sorbent material 102 may be heated, for example to typically 400° C., in order to evaporate the bound water and the bound nitrogen. This step may form an activation run and may be realized in an atmosphere of pure or essentially pure dry nitrogen in order to remove contaminants, such as water, and in order not to stress the respective components and thus to avoid oxidation reactions of the components. After cooling down to room temperature, for example, the sensor system, or its sorbent material, respectively, may be exposed to an oxygen atmosphere which will quickly purge out the nitrogen adsorbed in the sorbent material.

Figure 2:
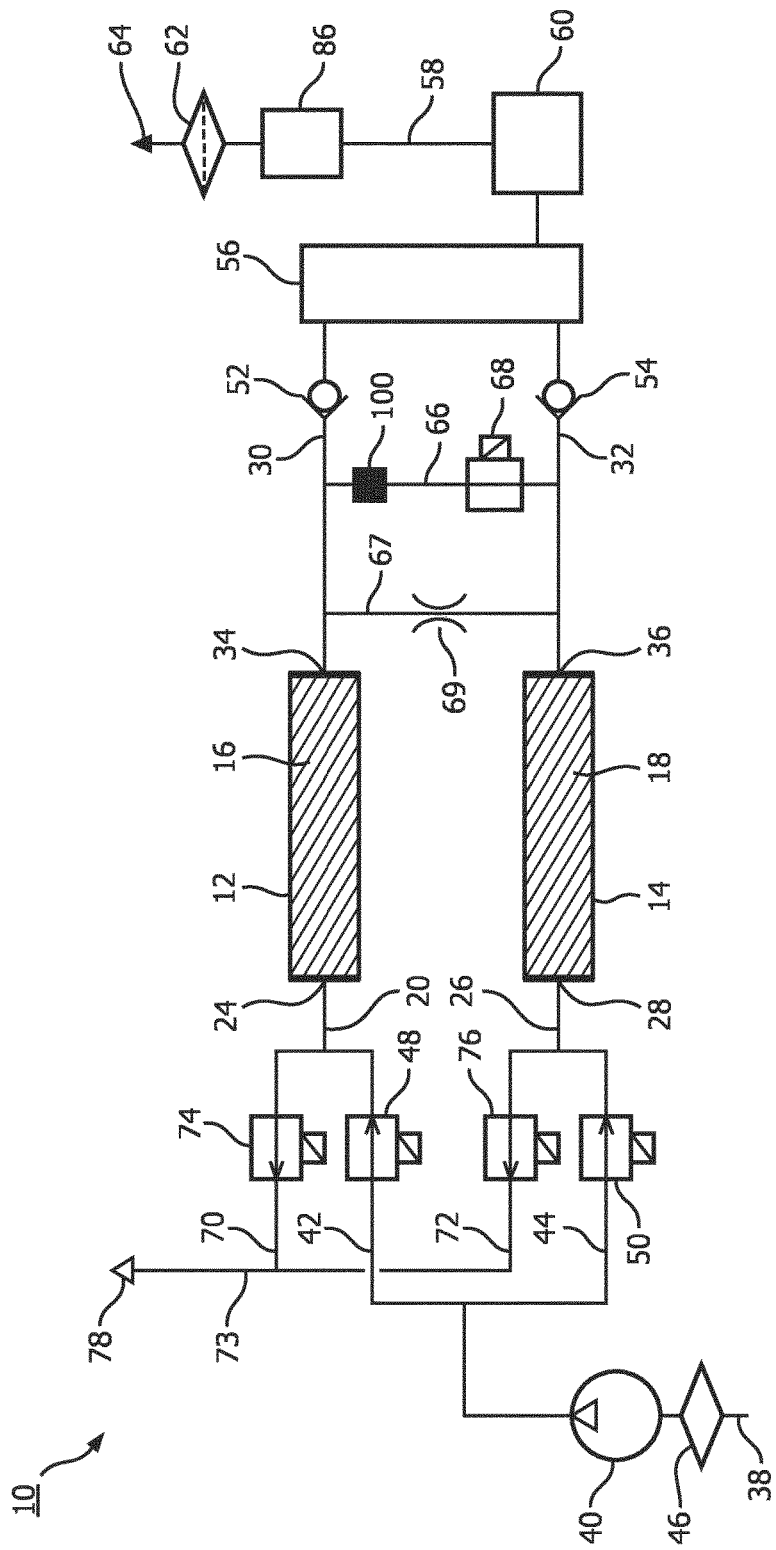
FIG. 2 shows a schematic view of an embodiment of an oxygen concentrator comprising a sensor system according to FIG. 1.

In FIG. 2, an exemplary embodiment of an oxygen separator 10 for generating oxygen is schematically shown. The oxygen separator 10 may be used for generating oxygen with respect to therapeutic applications, for example in the field of COPD treatment. The oxygen separator 10 may be designed as a stationary arrangement, for example for using it in a hospital, or it may be a portable device, for example for using it in the field of homecare applications. However, the oxygen separator 10 may furthermore be used for any application at which pure or essentially pure oxygen has to be provided, for example in air planes or for welding purposes. Such an oxygen concentrator, or oxygen separator 10, respectively, may be based on an oxygen concentrator such as the one called SimplyGo and which is purchasable from Philips Respironics.

The oxygen separator 10 according to FIG. 2 comprises at least one oxygen separation device 12 which is capable of separating oxygen from an oxygen comprising gas. However, it is preferred that the oxygen separator 10 comprises at least two oxygen separation devices 12, 14 being arranged in parallel. In the following, the invention is described with respect to two oxygen separation devices 12, 14. However, it is clear for one skilled in the art that every feature may be provided correspondingly by using just one oxygen separation device 12 or more than two oxygen separation devices 12, 14. Each oxygen separation device 12, 14 may be formed as a sieve bed and may be equipped with an oxygen separation sorbent 16, 18. The oxygen separation sorbent 16, 18 is particularly configured for letting oxygen pass without significantly impeding its flow, but for interacting with, or adsorbing, respectively other compounds being present in an oxygen comprising gas. In case air is used as oxygen comprising gas, it is thus preferred that the oxygen separation sorbent 16, 18 is configured for adsorbing nitrogen. Suitable oxygen separation sorbents 16, 18 may comprises a zeolite material such as a Li-LSX material. However it may be possible to use every suitable oxygen separation sorbent 16, 18 known in the art, for example for use in swing processes, such as pressure swing adsorption ore vacuum swing adsorption processes.

An inlet conduct 20 is provided for guiding a flow of oxygen comprising gas to the gas inlet 24 of the oxygen separation device 12 at its primary side. Correspondingly, an inlet conduct 26 is provided for guiding a flow of oxygen comprising gas to the gas inlet 28 of the oxygen separation device 14 at its primary side, respectively. Furthermore, outlet conducts 30, 32 for guiding oxygen enriched gas, or pure oxygen, respectively, out of the oxygen separation devices 12, 14 are connected to gas outlets 34, 36 of the respective oxygen separation device 12, 14.

The inlet conducts 24, 26 of the oxygen separation devices 12, 14 are connected to an inlet 38 of the oxygen separator 10. Connected to the inlet 38 is a source of oxygen comprising gas, such as a gas storing device or the air surrounding the oxygen separator 10. Additionally, a pressure adjusting device 40 for creating a pressure difference between the primary side and the secondary side of the oxygen separation device 12, 14 may be provided. According to FIG. 2, the pressure adjusting device 40 is formed as a compressor for compressing the oxygen comprising gas and forcing it through the inlet conducts 42, 44, which may be part of or connected to the inlet conducts 22, 26, to the oxygen separation devices 12, 14. Thus, according to the present invention, the expression an inlet conduct shall mean one, several or all of these inlet conducts 42, 44, 22, 26. Downstream or upstream the pressure adjusting device 40, an inlet filter 46 may be provided in order to provide a first cleaning step of the oxygen comprising gas. In detail, especially solid particles may be filtered out of the oxygen comprising gas.

In order to allow the oxygen comprising gas to be guided through the oxygen separation devices 12, 14 intermittently, inlet valves 48, 50 may be provided in the inlet conducts 42, 44. A valve according to the invention shall be any device which may allow a gas flow, inhibit a gas flow and/or regulate the amount of a gas flow. Consequently, by closing the valve 50 and by opening the valve 48, the oxygen comprising gas may be guided through the first oxygen separation device 12, whereas the oxygen comprising gas may be guided through the second oxygen separation device 14 by opening the valve 50 and by closing the valve 48. Correspondingly, a valve 52, such as a check valve, may be provided in the outlet conduct 30 and a valve 54, such as a check valve, may be provided in the outlet conduct 32. By guiding the oxygen comprising gas through the first oxygen separation device 12, the valve 52 may be opened whereas the valve 54 may be closed. Correspondingly, by guiding the oxygen comprising gas through the second oxygen separation device 14, the valve 54 may be opened whereas the valve 52 may be closed.

Downstream the valves 52, 54, the outlet conducts 30, 32 are connected to an oxygen accumulator 56, or a gas tank, respectively, in order to store the generated oxygen. The oxygen accumulator 56 may be connected to an outlet conduct 58 in which a flow controller 60 may be provided in order to control a stream of pure oxygen. Thus, according to the present invention, the expression an outlet conduct shall mean one, several or all of these outlet conducts 58, 30, 32. Furthermore, an additional filter 62 may be provided in the outlet conduct 58 before the generated oxygen is guided to an outlet 64. From the outlet 64, the generated oxygen enriched gas may be guided to the desired application, such as to a patient.

The outlet conduct 30 of the first oxygen separation device 12 and the outlet conduct 32 of the second oxygen separation device 14 may be connected by an equalization conduit 66 upstream the valves 52, 54, in which a valve 68, such as a two-way valve, which may be switched between an open and a closed position may be provided. This allows guiding a defined part of the generated oxygen, for example generated in the oxygen separation device 12, 14, to the further oxygen separation device 14, 12, or vice versa, for equalization purposes. In detail, in case the first oxygen separation device 12 is in an oxygen separation mode and the second oxygen separation device 14 is in a regeneration mode, or purge mode, respectively, the valve 68 may be opened allowing the overpressure of the first oxygen separation device 12 to be equalized with the pressure of the second oxygen separation device 14 thereby being guided through the equalization conduit 66 before changing the modes of the oxygen separation devices 12, 14. Thus, the equalization flow will go from oxygen separation device 12 to oxygen separation device 14 in one equalization phase and from oxygen separation device 14 to oxygen separation device 12 in the next equalization phase. The sensor system 100 may be provided in said equalization conduit 66.

Even though this is not problematic in most cases, in case the sorbent material 102 will be loaded with a too large amount of component to be detected, this component may be removed by simply purging it at ambient temperature, such as with oxygen in case the sorbent material 102 is sensitive for nitrogen, for example.

In vicinity to the equalization conduit, the outlet conduct 30 of the first oxygen separation device 12 and the outlet conduct 32 of the second oxygen separation device 14 may further be connected by a cross conduct 67 upstream the valves 52, 54, in which a flow regulator 69, such as an orifice or a flow controller, may be provided. This allows guiding a defined part of the generated oxygen, for example generated in the oxygen separation device 12, 14, back through the further oxygen separation device 14, 12, or vice versa, for purging purposes and thus for regenerating the oxygen separation devices 12, 14.

Further, the secondary side of the oxygen separation devices 12, 14 may be connected to a further source of purge gas, such as a tank comprising oxygen with a high purity, for example, for guiding the purge gas through the oxygen separation devices 12, 14, respectively. With this regard, exhaust conducts 70, 72 are provided at the primary sides of the oxygen separation devices 12, 14, each comprising a valve 74, 76. If purge gas, such as oxygen enriched gas, is guided through the oxygen separation devices 12, 14, from their secondary side to their primary side for regeneration purposes, the outflow may then be guided selectively through the exhaust conducts 70, 72. Further, the exhaust conducts 70, 72 may be guided each to an outlet or they may be combined to one common exhaust conduct 73 and may thus be guided to one common exhaust 78.

Although the sensor system 100 is developed specifically for use in the equalization conduit 66 in case it is used in the oxygen concentrator 10, it is not limited thereto. It can for instance be used in the hose that delivers oxygen to the patient.

Figure 3:
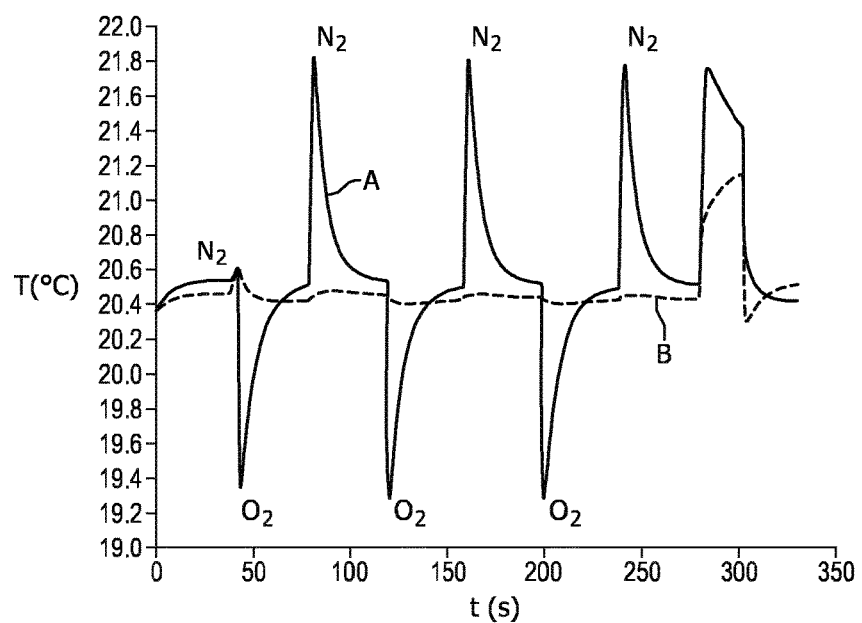
FIG. 3 shows a diagram of measuring results obtained with a sensor system according to FIG. 1.

FIG. 3 shows a schematic and exemplary measurement of a sensor system 100 with compounds present in the oxygen concentrator 10. In fact, the time in seconds (t(s)) is shown against temperature in degrees Celsius (T (° C.)). Line A thereby corresponds to the first temperature sensor 104 measuring the temperature of the sorbent material 102, whereas line B corresponds to the second temperature sensor 105 measuring the atmosphere surrounding the sorbent material 102. The sorbent material 102 used is thereby a sorbent which is sensitive for nitrogen and thus undergoes a temperature rise when sorbing nitrogen. It can be seen that that a change of the atmosphere surrounding the sorbent material 102 is directly detectable by a temperature change. In fact, changing the atmosphere from oxygen to nitrogen is detectable by a temperature rise, or peak, respectively, of the first temperature sensor 104. In contrast thereto, changing the atmosphere from nitrogen to oxygen is detectable by a temperature fall, or valley, respectively, of the first temperature sensor 104. In other words, in case the sorbent material 102 is in pure oxygen or oxygen enriched gas and some nitrogen will arise, this is directly detectable by a temperature rise by the first temperature sensor 104.

FIG. 3 further shows the temperature measured by the second temperature sensor 105 (line B). It is thereby also shown that a pressure rise e.g. from 1 bar to 1.9 bar, shown at approximately 300 s, can be detected since that gives a peak on the second temperature sensor 105, or reference temperature sensor, respectively, The signal of the second temperature sensor 105 can thus be used to compensate for effect of pressure differences, for example.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An oxygen concentrator for generating oxygen enriched gas, comprising:
   a sensor system for quantitatively detecting nitrogen in an oxygen comprising gas, said gas comprising nitrogen, wherein the sensor system comprises:
      a zeolite capable of absorbing nitrogen, wherein the zeolite undergoes a temperature change when absorbing nitrogen;
      at least a first temperature sensor for measuring the temperature of the zeolite; and
      a control unit being adapted for quantitatively determining nitrogen based on the temperature change of the zeolite relative to a temperature change of the gas, and for dynamically controlling an oxygen separation device in dependence on the result of the quantitatively determined nitrogen.

2. The oxygen concentrator according to claim 1, wherein the sensor system further comprises a second temperature sensor for measuring the temperature of the gas.

3. The oxygen concentrator according to claim 1, wherein the zeolite is provided on a surface of the first temperature sensor.

4. The oxygen concentrator according to claim 2, wherein the second temperature sensor comprises a thermistor or a thermocouple.

5. The oxygen concentrator according to claim 1, wherein a heating device is provided for heating the zeolite.

6. The oxygen concentrator according to claim 1, wherein the zeolite of the sensor system is provided in an equalization conduit.

7. A method of controlling an oxygen separation device by quantitatively detecting nitrogen in an oxygen comprising gas, said gas comprising the nitrogen, wherein the method comprises the steps of:
   absorbing the nitrogen in a zeolite, wherein the zeolite undergoes a temperature change when absorbing the nitrogen;
   measuring the temperature of the zeolite;
   quantitatively detecting the nitrogen based on the temperature change of the zeolite relative to a temperature change of the gas; and
   dynamically controlling the oxygen separation device in dependence on the result of the quantitatively detected nitrogen.

8. The method according to claim 7, wherein the method is part of a method for separating oxygen from the oxygen comprising gas.

9. The method according to claim 7, wherein nitrogen is detected during an equalization phase of a Pressure Swing Adsorption, PSA, cycle.

10. The method according to claim 7 further comprising:
measuring, by a second temperature sensor, a temperature of the gas, wherein the second temperature sensor comprises a thermistor or a thermocouple.

* * * * *